US012637459B2

(12) United States Patent
Przeczkova et al.

(10) Patent No.: US 12,637,459 B2
(45) Date of Patent: May 26, 2026

(54) SOLID STATE FORMS OF LORECIVIVINT

(71) Applicant: TAPI CZECH INDUSTRIES S.R.O., Opava-komarov (CZ)

(72) Inventors: Zuzana Przeczkova, Ostrava (CZ); Adéla Bártová, Ostrava-Michalkovice (CZ); Pavel Kolesa, Hlubocec (CZ); Alexandr Jegorov, Dobra Voda (CZ)

(73) Assignee: TAPI CZECH INDUSTRIES S.R.O, Opava-komarov (CZ)

( * ) Notice: Subject to any disclaimer, the term of this patent is extended or adjusted under 35 U.S.C. 154(b) by 636 days.

(21) Appl. No.: 18/030,785

(22) PCT Filed: Oct. 12, 2021

(86) PCT No.: PCT/US2021/054465
§ 371 (c)(1),
(2) Date: Apr. 7, 2023

(87) PCT Pub. No.: WO2022/081502
PCT Pub. Date: Apr. 21, 2022

(65) Prior Publication Data

US 2023/0373998 A1 Nov. 23, 2023

Related U.S. Application Data

(60) Provisional application No. 63/157,900, filed on Mar. 8, 2021, provisional application No. 63/120,440, filed on Dec. 2, 2020, provisional application No. 63/090,833, filed on Oct. 13, 2020.

(51) Int. Cl.
*C07D 471/04* (2006.01)

(52) U.S. Cl.
CPC .................................. *C07D 471/04* (2013.01)

(58) Field of Classification Search
None
See application file for complete search history.

(56) References Cited

U.S. PATENT DOCUMENTS 10,633,380 B2 * 4/2020 Kc .......................... A61P 35/00

FOREIGN PATENT DOCUMENTS

| | | | | |
|---|---|---|---|---|
| WO | 2013151708 | A1 | 10/2013 | |
| WO | 2017079765 | A1 | 5/2017 | |
| WO | WO-2017079759 | A1 * | 5/2017 | ......... A61K 31/4545 |
| WO | 2017210407 | A1 | 12/2017 | |
| WO | 2018085865 | A1 | 5/2018 | |

OTHER PUBLICATIONS

Decision on Rejection issued in corresponding application CN 202180070170.5 dated Oct. 9, 2025, together with English language machine translation.
Office Action issued in corresponding Chinese Application 202180070170.5 mailed May 31, 2025, together with English language translation obtained from the Global dossier.
International Search Report and Written Opinion of the International Searching Authority issued in corresponding application PCT/US2021/054465 mailed Mar. 1, 2022 (14 pages).

* cited by examiner

*Primary Examiner* — Jeffrey S Lundgren
*Assistant Examiner* — Sara Elizabeth Townsley
(74) *Attorney, Agent, or Firm* — Carter, DeLuca & Farrell LLP

(57) ABSTRACT

The present disclosure encompasses solid state forms of Lorecivivint, in embodiments crystalline polymorphs of Lorecivivint, processes for preparation thereof, and pharmaceutical compositions thereof.

13 Claims, 9 Drawing Sheets an X-ray powder diffractogram (XRPD) of crystalline form Q of Lorecivivint.

Figure 1. an X-ray powder diffractogram (XRPD) of crystalline form C of Lorecivivint.
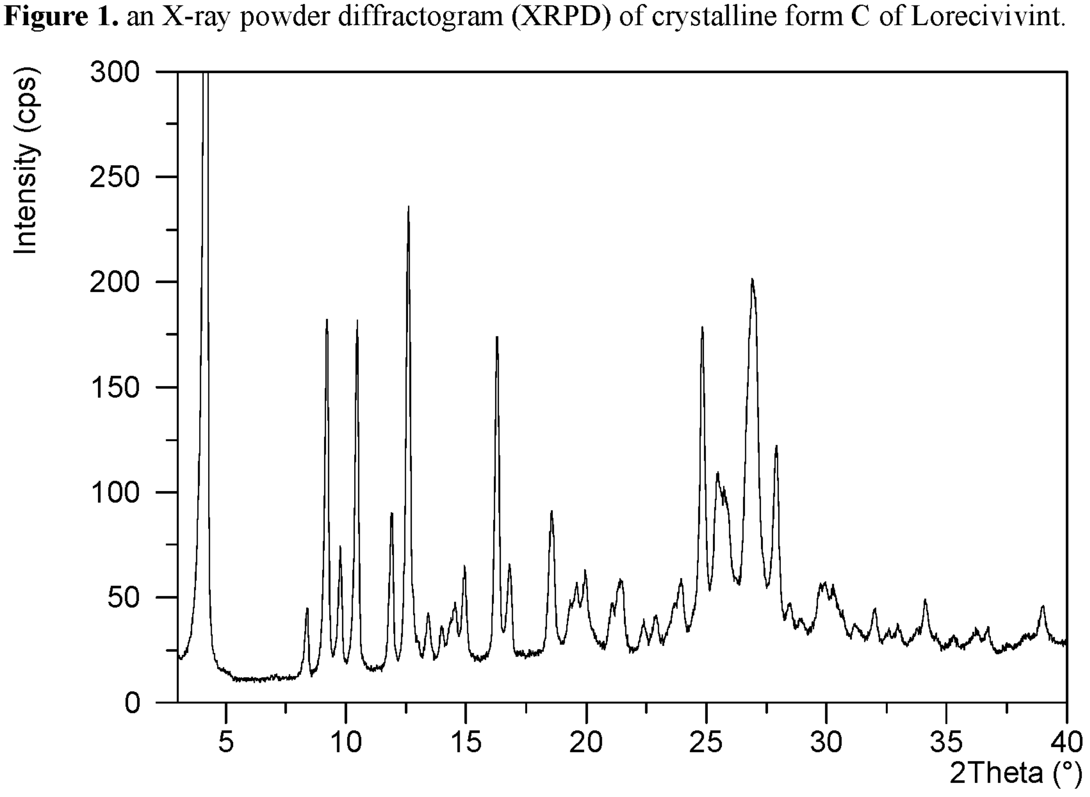

Figure 2. an X-ray powder diffractogram (XRPD) of crystalline form F of Lorecivivint.
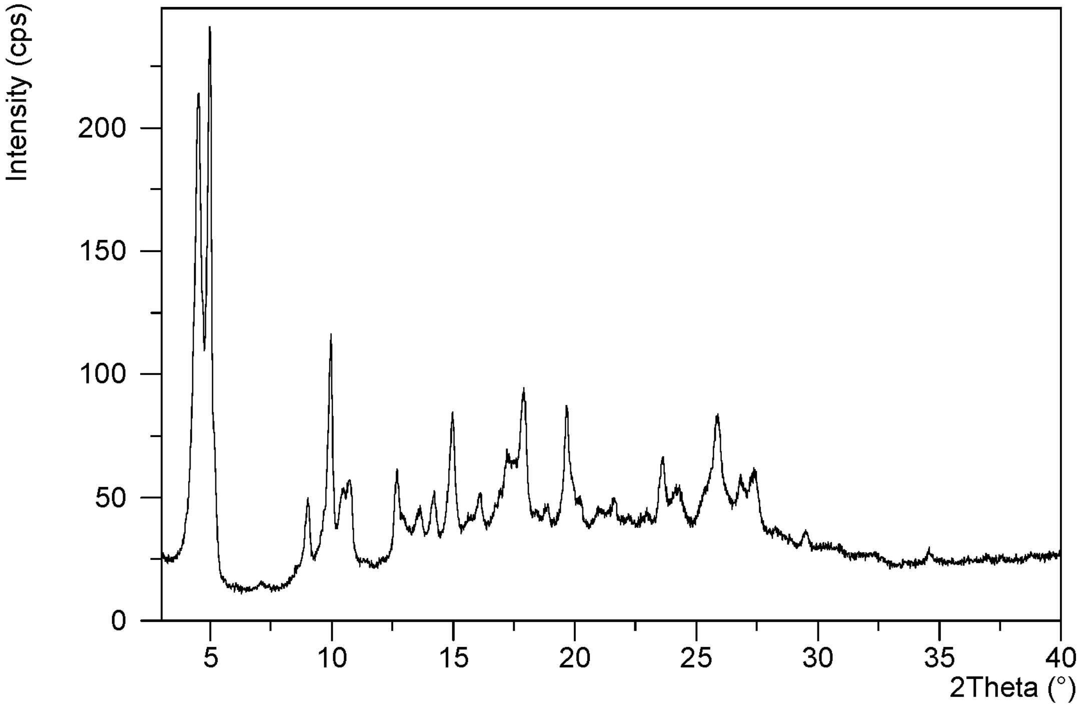

Figure 3. an X-ray powder diffractogram (XRPD) of crystalline form H of Lorecivivint.
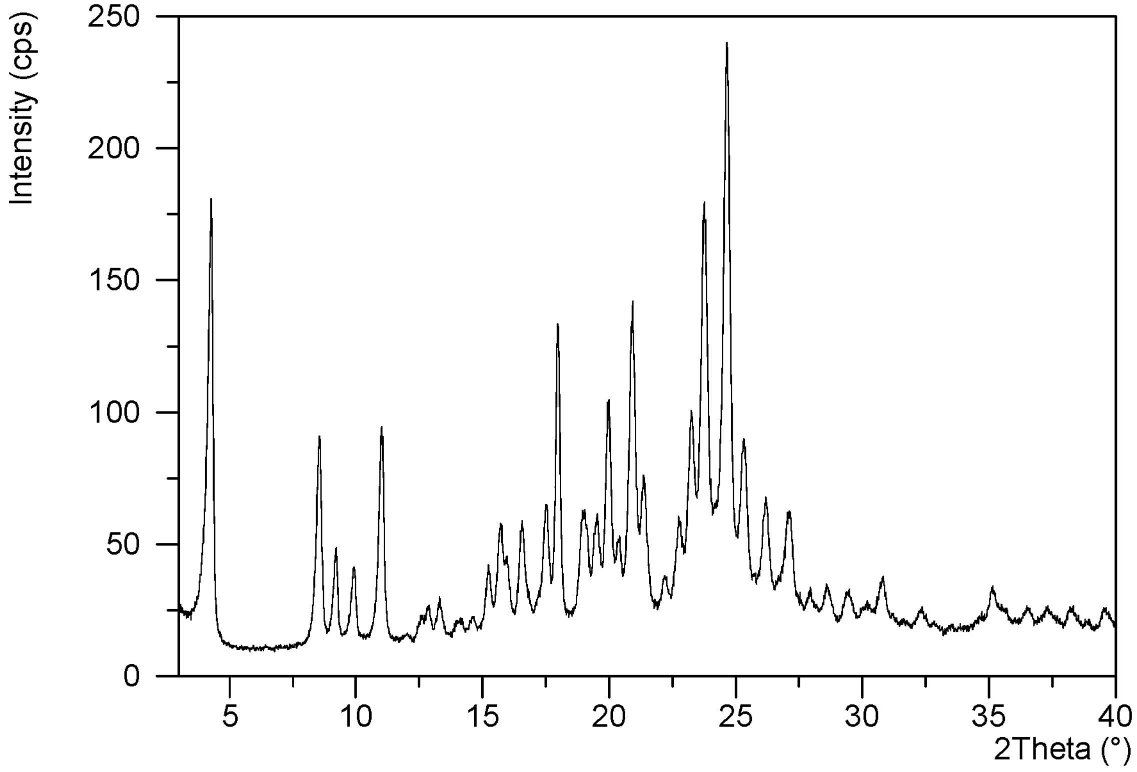

Figure 4. an X-ray powder diffractogram (XRPD) of amorphous Lorecivivint.
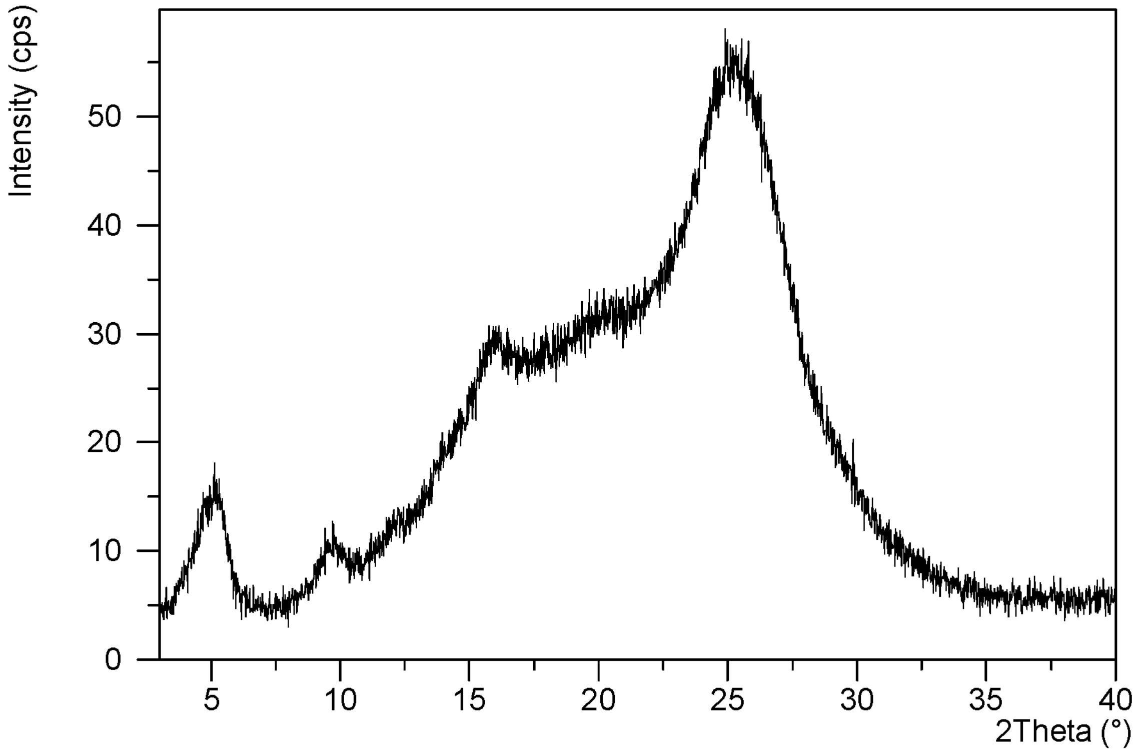

Figure 5. an X-ray powder diffractogram (XRPD) of crystalline form Q of Lorecivivint.
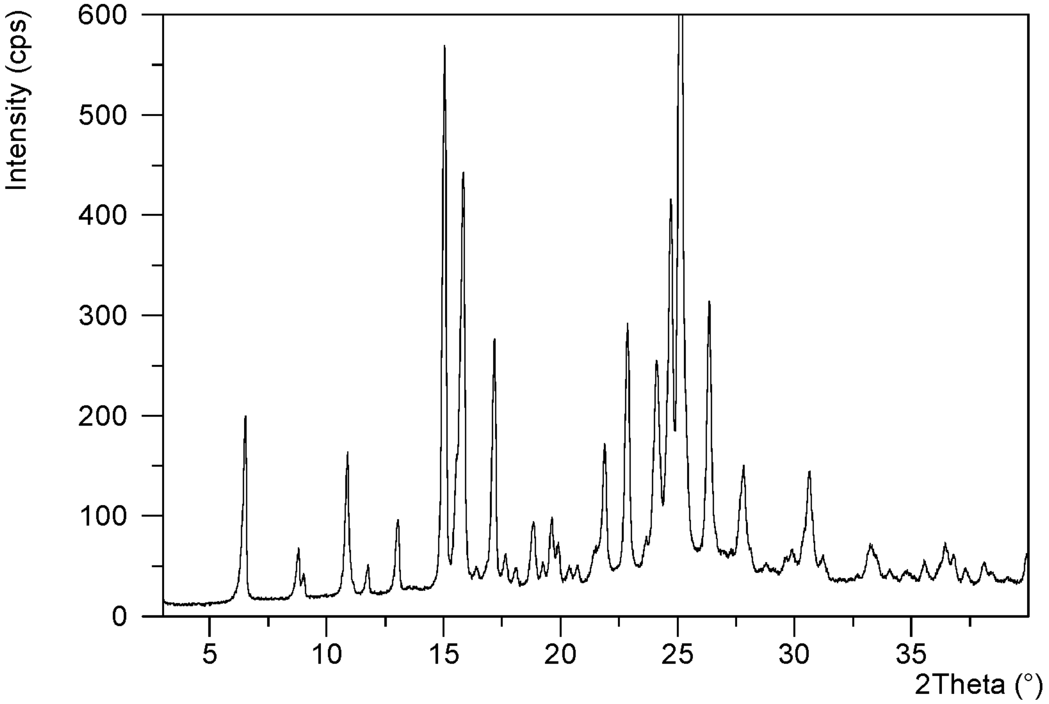

Figure 6. A characteristic solid state $^{13}C$ NMR spectrum of form Q of Lorecivivint (full range 200-0 ppm)
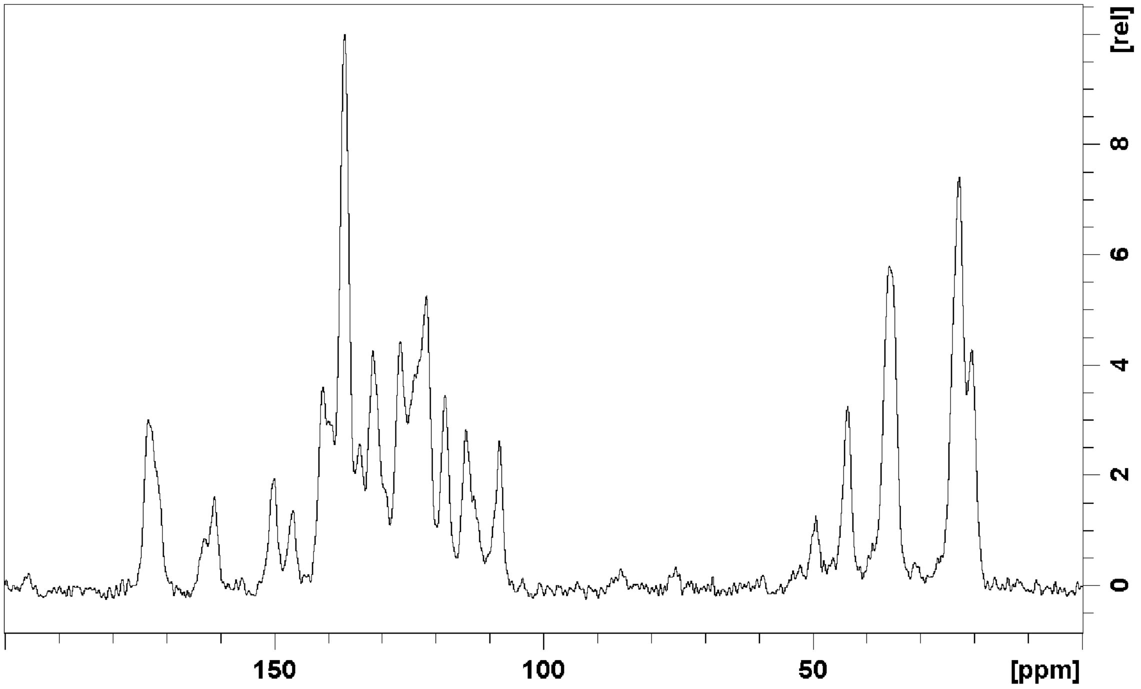

Figure 7. A characteristic solid state $^{13}C$ NMR spectrum of form Q of Lorecivivint (200-100 ppm)
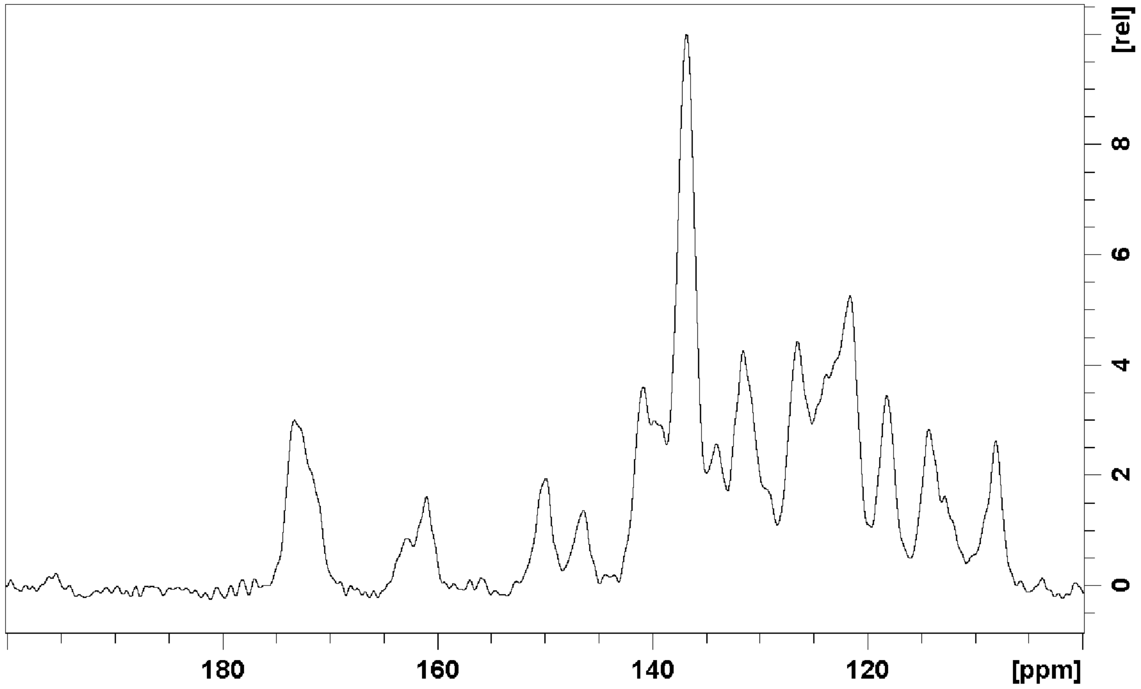

Figure 8. A characteristic solid state $^{13}C$ NMR spectrum of form Q of Lorecivivint (100-0 ppm)
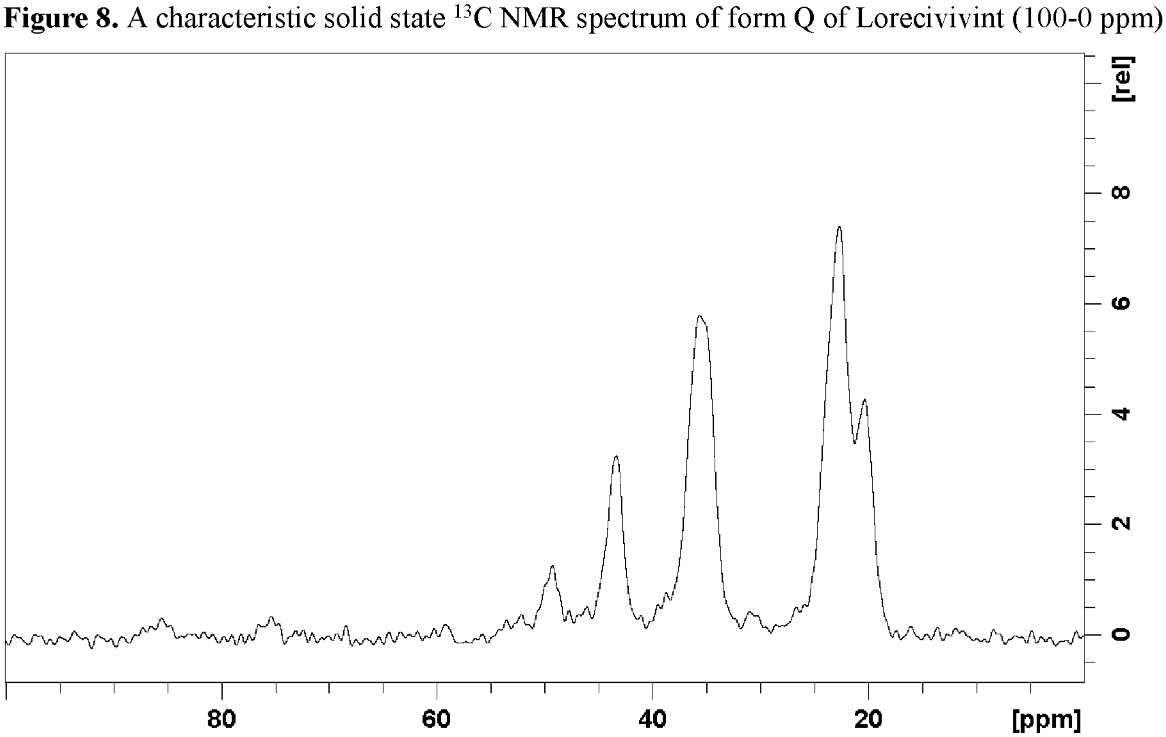

Figure 9. X-ray powder diffraction pattern (XRPD) of Lorecivivint Form Q obtained by procedure C of Example 5
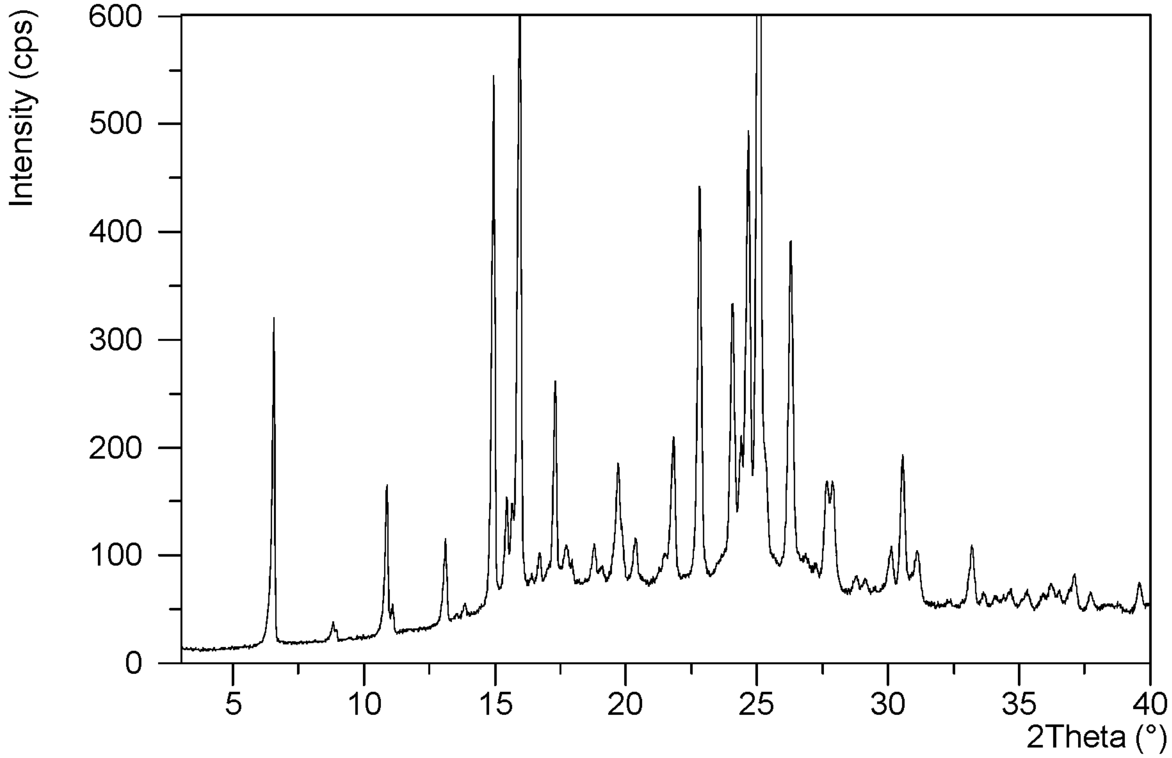

SOLID STATE FORMS OF LORECIVIVINT

FIELD OF THE DISCLOSURE

The present disclosure encompasses solid state forms of Lorecivivint, in embodiments crystalline polymorphs of Lorecivivint, processes for preparation thereof, and pharmaceutical compositions thereof.

BACKGROUND OF THE DISCLOSURE

Lorecivivint, N-[5-[3-[7-(3-fluorophenyl)-3H-imidazo[4,5-c]pyridin-2-yl]-1H-indazol-5-yl]pyridin-3-yl]-3-methylbutanamide, has the following chemical structure:

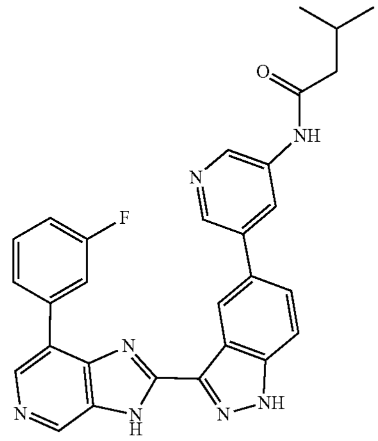 [SMILES: CC(C)CC(=O)Nc1cncc(-c2ccc3[nH]nc(-c4nc5c(-c6cccc(F)c6)cncc5[nH]4)c3c2)c1]

Lorecivivint is an investigational CLK/DYRK1A inhibitor that modulates the Wnt pathway, and it is developed for the treatment of knee osteoarthritis.

The compound is described in International Publication No. WO 2013/151708. International Publication Nos. WO 2017/079765 and WO 2017/079759 disclose crystalline forms of Lorecivivint and International Publication No. WO 2017/210407 discloses processes for preparation thereof.

Polymorphism, the occurrence of different crystalline forms, is a property of some molecules and molecular complexes. A single molecule may give rise to a variety of polymorphs having distinct crystal structures and physical properties like melting point, thermal behaviors (e.g., measured by thermogravimetric analysis ("TGA"), or differential scanning calorimetry ("DSC")), X-ray diffraction (XRD) pattern, infrared absorption fingerprint, and solid state ($^{13}C$) NMR spectrum. One or more of these techniques may be used to distinguish different polymorphic forms of a compound.

Different salts and solid state forms (including solvated forms) of an active pharmaceutical ingredient may possess different properties. Such variations in the properties of different salts and solid state forms and solvates may provide a basis for improving formulation, for example, by facilitating better processing or handling characteristics, changing the dissolution profile in a favorable direction, or improving stability (polymorph as well as chemical stability) and shelf-life. These variations in the properties of different salts and solid state forms may also offer improvements to the final dosage form, for instance, if they serve to improve bioavailability. Different salts and solid state forms and solvates of an active pharmaceutical ingredient may also give rise to a variety of polymorphs or crystalline forms, which may in turn provide additional opportunities to assess variations in the properties and characteristics of a solid active pharmaceutical ingredient.

Discovering new solid state forms and solvates of a pharmaceutical product may yield materials having desirable processing properties, such as ease of handling, ease of processing, storage stability, and ease of purification or as desirable intermediate crystal forms that facilitate conversion to other polymorphic forms. New solid state forms of a pharmaceutically useful compound can also provide an opportunity to improve the performance characteristics of a pharmaceutical product. It enlarges the repertoire of materials that a formulation scientist has available for formulation optimization, for example by providing a product with different properties, including a different crystal habit, higher crystallinity, or polymorphic stability, which may offer better processing or handling characteristics, improved dissolution profile, or improved shelf-life (chemical/physical stability). For at least these reasons, there is a need for additional solid state forms (including solvated forms) of Lorecivivint.

SUMMARY OF THE DISCLOSURE

The present disclosure provides crystalline polymorphs of Lorecivivint, processes for preparation thereof, and pharmaceutical compositions thereof. These crystalline polymorphs can be used to prepare other solid state forms of Lorecivivint, Lorecivivint salts and their solid state forms.

The present disclosure also provides uses of the said solid state forms of Lorecivivint in the preparation of other solid state forms of Lorecivivint or salts thereof.

The present disclosure provides crystalline polymorphs of Lorecivivint for use in medicine, including for the treatment of knee osteoarthritis.

The present disclosure also encompasses the use of crystalline polymorphs of Lorecivivint of the present disclosure for the preparation of pharmaceutical compositions and/or formulations.

In another aspect, the present disclosure provides pharmaceutical compositions comprising crystalline polymorphs of Lorecivivint according to the present disclosure.

The present disclosure includes processes for preparing the above mentioned pharmaceutical compositions. The processes include combining any one or a combination of the crystalline polymorphs of Lorecivivint with at least one pharmaceutically acceptable excipient.

The crystalline polymorphs of Lorecivivint as defined herein and the pharmaceutical compositions or formulations of the crystalline polymorphs of Lorecivivint may be used as medicaments, such as for the treatment of knee osteoarthritis.

The present disclosure also provides methods of treating knee osteoarthritis, by administering a therapeutically effective amount of any one or a combination of the crystalline polymorphs of Lorecivivint of the present disclosure, or at least one of the above pharmaceutical compositions, to a subject suffering from knee osteoarthritis, or otherwise in need of the treatment.

The present disclosure also provides uses of crystalline polymorphs of Lorecivivint of the present disclosure, or at least one of the above pharmaceutical compositions, for the manufacture of medicaments for treating e.g., knee osteoarthritis.

BRIEF DESCRIPTION OF THE DRAWINGS

FIG. 1 shows a characteristic X-ray powder diffraction pattern (XRPD) of Lorecivivint Form C.

FIG. 2 shows a characteristic X-ray powder diffraction pattern (XRPD) of Lorecivivint Form F.

FIG. 3 shows a characteristic X-ray powder diffraction pattern (XRPD) of Lorecivivint Form H.

FIG. 4 shows a characteristic X-ray powder diffraction pattern (XRPD) of amorphous Lorecivivint.

FIG. 5 shows a characteristic X-ray powder diffraction pattern (XRPD) of Lorecivivint Form Q.

FIG. 6 shows a characteristic solid state $^{13}C$ NMR spectrum of form Q of Lorecivivint (full range 200-0 ppm).

FIG. 7 shows a characteristic solid state $^{13}C$ NMR spectrum of form Q of Lorecivivint (200-100 ppm).

FIG. 8 shows a characteristic solid state $^{13}C$ NMR spectrum of form Q of Lorecivivint (100-0 ppm).

FIG. 9 shows an X-ray powder diffraction pattern (XRPD) of Lorecivivint Form Q obtained by procedure C of Example 5.

DETAILED DESCRIPTION OF THE DISCLOSURE

The present disclosure encompasses solid state forms of Lorecivivint, including crystalline polymorphs of Lorecivivint, processes for preparation thereof, and pharmaceutical compositions thereof.

Solid state properties of Lorecivivint and crystalline polymorphs thereof can be influenced by controlling the conditions under which Lorecivivint and crystalline polymorphs thereof are obtained in solid form.

A solid state form (or polymorph) may be referred to herein as polymorphically pure or as substantially free of any other solid state (or polymorphic) forms. As used herein in this context, the expression "substantially free of any other forms" will be understood to mean that the solid state form contains about 20% (w/w) or less, about 10% (w/w) or less, about 5% (w/w) or less, about 2% (w/w) or less, about 1% (w/w) or less, or about 0% of any other forms of the subject compound as measured, for example, by XRPD. Thus, a crystalline polymorph of Lorecivivint described herein as substantially free of any other solid state forms would be understood to contain greater than about 80% (w/w), greater than about 90% (w/w), greater than about 95% (w/w), greater than about 98% (w/w), greater than about 99% (w/w), or about 100% of the subject crystalline polymorph of Lorecivivint. In some embodiments of the disclosure, the described crystalline polymorph of Lorecivivint may contain from about 1% to about 20% (w/w), from about 5% to about 20% (w/w), or from about 5% to about 10% (w/w) of one or more other crystalline polymorph of the same Lorecivivint.

Depending on which other crystalline polymorphs a comparison is made, the crystalline polymorphs of Lorecivivint of the present disclosure may have advantageous properties selected from at least one of the following: chemical purity, flowability, solubility, dissolution rate, morphology or crystal habit, stability, such as chemical stability as well as thermal and mechanical stability with respect to polymorphic conversion, stability towards dehydration and/or storage stability, low content of residual solvent, a lower degree of hygroscopicity, flowability, and advantageous processing and handling characteristics such as compressibility and bulk density.

A solid state form, such as a crystal form or an amorphous form, may be referred to herein as being characterized by graphical data "as depicted in" or "as substantially depicted in" a Figure. Such data include, for example, powder X-ray diffractograms and solid state NMR spectra. As is well-known in the art, the graphical data potentially provides additional technical information to further define the respective solid state form (a so-called "fingerprint") which cannot necessarily be described by reference to numerical values or peak positions alone. In any event, the skilled person will understand that such graphical representations of data may be subject to small variations, e.g., in peak relative intensities and peak positions due to certain factors such as, but not limited to, variations in instrument response and variations in sample concentration and purity, which are well known to the skilled person. Nonetheless, the skilled person would readily be capable of comparing the graphical data in the Figures herein with graphical data generated for an unknown crystal form and confirm whether the two sets of graphical data are characterizing the same crystal form or two different crystal forms. A crystal form of Lorecivivint referred to herein as being characterized by graphical data "as depicted in" or "as substantially depicted in" a Figure will thus be understood to include any crystal forms of Lorecivivint characterized with the graphical data having such small variations, as are well known to the skilled person, in comparison with the Figure.

As used herein, and unless stated otherwise, the term "anhydrous" in relation to crystalline forms of Lorecivivint, relates to a crystalline form of Lorecivivint which does not include any crystalline water (or other solvents) in a defined, stoichiometric amount within the crystal. Moreover, an "anhydrous" form would generally not contain more than 1% (w/w), of either water or organic solvents as measured for example by TGA.

The term "solvate," as used herein and unless indicated otherwise, refers to a crystal form that incorporates a solvent in the crystal structure. When the solvent is water, the solvate is often referred to as a "hydrate." The solvent in a solvate may be present in either a stoichiometric or in a non-stoichiometric amount.

As used herein, the term "isostructural" or "isostructure", refers to two or more solid forms of a compound containing essentially the same three-dimensional arrangement of geometrically similar structural units. In some embodiments, "isostructural" forms show with similar or identical unit cell dimensions, the same space group, and similar or identical atomic coordinates for common atoms. In some embodiments, "isostructural" forms have the same structure, but not the same cell dimensions nor the same chemical composition, and have comparable variability in their atomic coordinates to that of the cell dimensions and chemical composition.

As used herein, the term "isolated" in reference to crystalline polymorph of Lorecivivint of the present disclosure corresponds to a crystalline polymorph of Lorecivivint that is physically separated from the reaction mixture in which it is formed.

As used herein, unless stated otherwise, the XRPD measurements are taken using copper K$\alpha$ radiation wavelength 1.5418 Å. XRPD peaks reported herein are measured using CuK $\alpha$ radiation, $\lambda$=1.54187 Å, typically at a temperature of 25±3° C.

As used herein, unless stated otherwise, $^{13}C$ NMR measurements are obtained at 125 MHz at a magic angle spinning (MAS) frequency $\omega r/2\pi$=11 kHz.

As used herein, unless stated otherwise, TGA analysis is carried out at a heating rate of 10° C./min to 250° C., preferably with a nitrogen flow of 25 ml/minute.

A thing, e.g., a reaction mixture, may be characterized herein as being at, or allowed to come to "room temperature" or "ambient temperature", often abbreviated as "RT."

This means that the temperature of the thing is close to, or the same as, that of the space, e.g., the room or fume hood, in which the thing is located. Typically, room temperature is from about 20° C. to about 30° C., or about 22° C. to about 27° C., or about 25° C.

The amount of solvent employed in a chemical process, e.g., a reaction or crystallization, may be referred to herein as a number of "volumes" or "vol" or "V." For example, a material may be referred to as being suspended in 10 volumes (or 10 vol or 10 V) of a solvent. In this context, this expression would be understood to mean milliliters of the solvent per gram of the material being suspended, such that suspending a 5 grams of a material in 10 volumes of a solvent means that the solvent is used in an amount of 10 milliliters of the solvent per gram of the material that is being suspended or, in this example, 50 mL of the solvent. In another context, the term "v/v" may be used to indicate the number of volumes of a solvent that are added to a liquid mixture based on the volume of that mixture. For example, adding solvent X (1.5 v/v) to a 100 ml reaction mixture would indicate that 150 mL of solvent X was added.

A process or step may be referred to herein as being carried out "overnight." This refers to a time interval, e.g., for the process or step, that spans the time during the night, when that process or step may not be actively observed. This time interval is from about 8 to about 20 hours, or about 10-18 hours, in some cases about 16 hours.

As used herein, the term "reduced pressure" refers to a pressure that is less than atmospheric pressure. For example, reduced pressure is about 10 mbar to about 50 mbar.

As used herein and unless indicated otherwise, the term "ambient conditions" refer to atmospheric pressure and a temperature of 22-24° C.

The present disclosure includes a crystalline polymorph of Lorecivivint, designated form C. The crystalline Form C of Lorecivivint may be characterized by data selected from one or more of the following: an X-ray powder diffraction pattern substantially as depicted in FIG. 1; an X-ray powder diffraction pattern having peaks at 4.2, 9.2, 10.5, 12.0 and 12.6 degrees 2-theta±0.2 degrees 2-theta; and combinations of these data.

Crystalline Form C of Lorecivivint may be further characterized by an X-ray powder diffraction pattern having peaks at 4.2, 9.2, 10.5, 12.0 and 12.6 degrees 2-theta+0.2 degrees 2-theta, and also having any one, two, three or four additional peaks selected from 8.4, 9.8, 16.3, 18.6 and 24.9 degrees 2-theta±0.2 degrees 2-theta.

Crystalline form C may be alternatively characterized by an X-ray powder diffraction pattern having peaks at 4.2, 8.4, 9.2, 9.8, 10.5, 12.0, 12.6, 16.3, 18.6 and 24.9 degrees 2-theta 0.2 degrees 2-theta.

In one embodiment of the present disclosure, crystalline Form C of Lorecivivint is isolated. Particularly, crystalline form C of Lorecivivint according to any aspect or embodiment of the disclosure may be isolated.

Crystalline form C may be a methanol solvate.

Crystalline Form C of Lorecivivint may be characterized by each of the above characteristics alone/or by all possible combinations, e.g., an XRPD pattern having peaks at 4.2, 9.2, 10.5, 12.0 and 12.6 degrees 2-theta±0.2 degrees 2-theta; an XRPD pattern as depicted in FIG. 1, and combinations thereof.

The present disclosure includes a crystalline polymorph of Lorecivivint, designated form F. The crystalline Form F of Lorecivivint may be characterized by data selected from one or more of the following: an X-ray powder diffraction pattern substantially as depicted in FIG. 2; an X-ray powder diffraction pattern having peaks at 4.6, 5.0, 9.0, 9.9 and 14.9 degrees 2-theta±0.2 degrees 2-theta; and combinations of these data.

Crystalline Form F of Lorecivivint may be further characterized by an X-ray powder diffraction pattern having peaks at 4.6, 5.0, 9.0, 9.9 and 14.9 degrees 2-theta±0.2 degrees 2-theta, and also having any one, two, three or four additional peaks selected from 12.7, 14.2, 17.8, 19.6 and 23.6 degrees 2-theta±0.2 degrees 2-theta.

Crystalline Form F may be alternatively characterized by an X-ray powder diffraction pattern having peaks at 4.6, 5.0, 9.0, 9.9, 12.7, 14.2, 14.9, 17.8, 19.6 and 23.6 degrees 2-theta 0.2 degrees 2-theta.

In one embodiment of the present disclosure, crystalline Form F of Lorecivivint is isolated. Particularly, crystalline form F of Lorecivivint according to any aspect or embodiment of the disclosure may be isolated.

Crystalline Form F of Lorecivivint may be characterized by each of the above characteristics alone/or by all possible combinations, e.g., an XRPD pattern having peaks at 4.6, 5.0, 9.0, 9.9 and 14.9 degrees 2-theta±0.2 degrees 2-theta; an XRPD pattern as depicted in FIG. 2, and combinations thereof.

The present disclosure includes a crystalline polymorph of Lorecivivint, designated Form H. The crystalline Form H of Lorecivivint may be characterized by data selected from one or more of the following: an X-ray powder diffraction pattern substantially as depicted in FIG. 3; an X-ray powder diffraction pattern having peaks at 4.2, 8.5, 9.2, 9.9 and 11.0 degrees 2-theta±0.2 degrees 2-theta; and combinations of these data.

Crystalline Form H of Lorecivivint may be further characterized by an X-ray powder diffraction pattern having peaks at 4.2, 8.5, 9.2, 9.9 and 11.0 degrees 2-theta±0.2 degrees 2-theta, and also having any one, two, three or four additional peaks selected from 16.6, 17.5, 18.0, 20.9 and 24.6 degrees 2-theta±0.2 degrees 2-theta.

Crystalline Form H may be alternatively characterized by an X-ray powder diffraction pattern having peaks at 4.2, 8.5, 9.2, 9.9, 11.0, 16.6, 17.5, 18.0, 20.9 and 24.6 degrees 2-theta±0.2 degrees 2-theta.

In one embodiment of the present disclosure, crystalline Form H of Lorecivivint is isolated. Particularly, crystalline form H of Lorecivivint according to any aspect or embodiment of the disclosure may be isolated.

Crystalline form H may be a mixed dioxane solvate and hydrate.

Crystalline Form H of Lorecivivint may be characterized by each of the above characteristics alone/or by all possible combinations, e.g., an XRPD pattern having peaks at 4.2, 8.5, 9.2, 9.9 and 11.0 degrees 2-theta±0.2 degrees 2-theta; an XRPD pattern as depicted in FIG. 3, and combinations thereof.

The present disclosure includes a crystalline polymorph of Lorecivivint, designated Form Q. The crystalline Form Q of Lorecivivint may be characterized by data selected from one or more of the following: an X-ray powder diffraction pattern substantially as depicted in FIG. 5; an X-ray powder diffraction pattern having peaks at 10.9, 17.2, 21.9, 22.9 and 25.2 degrees 2-theta±0.2 degrees 2-theta; a solid state $^{13}C$ NMR spectrum with characteristic peaks at 173.3, 149.9, 134.0, 131.5 and 118.2 ppm±0.2 ppm; a solid state $^{13}C$ NMR spectrum having the following chemical shift absolute differences from reference peak at 108.0 ppm±1 ppm: 65.3, 41.9 26.0, 23.5 and 10.2 ppm±0.1 ppm; a solid state $^{13}C$ NMR spectrum substantially as depicted in FIG. 6, 7 or 8; and combinations of these data.

Crystalline Form Q of Lorecivivint may be further characterized by an X-ray powder diffraction pattern having peaks at 10.9, 17.2, 21.9, 22.9 and 25.2 degrees 2-theta+0.2 degrees 2-theta, and also having any one, two, three, four or five additional peaks selected from 8.8, 11.8, 13.1, 18.9 and 24.1 degrees 2-theta+0.2 degrees 2-theta.

Crystalline form Q of Lorecivivint may be alternatively characterized by X-ray powder diffraction pattern having peaks at 8.8, 10.9, 11.8, 13.1, 17.2, 18.9, 21.9, 22.9, 24.1 and 25.2 degrees 2-theta±0.2 degrees 2-theta.

Alternatively, or in addition to the above, Form Q of Lorecivivint may be characterized by the following unit cell data:

a=13.497 Å
b=19.557 Å
c=11.701 Å
β=90.744°
cell_volume 3088 $Å^3$
Space group $P2_1/c$
At 298 K.

In one embodiment of the present disclosure, crystalline Form Q of Lorecivivint is isolated. Particularly, crystalline form Q of Lorecivivint according to any aspect or embodiment of the disclosure may be isolated.

Crystalline Form Q of Lorecivivint may be characterized by each of the above characteristics alone or by all possible combinations, e.g., an XRPD pattern having peaks at 10.9, 17.2, 21.9, 22.9 and 25.2 degrees 2-theta±0.2 degrees 2-theta; an XRPD pattern as depicted in FIG. 5, and combinations thereof.

In embodiments, crystalline form Q of Lorecivivint may be a mixed dimethylacetamide solvate hydrate, preferably a mono dimethylacetamide solvate and/or mono hydrate. In embodiments, crystalline form Q of Lorecivivint may contain about 13% to about 17% of dimethylacetamide and about 2% to about 5% of water, specifically, about 15% of dimethylacetamide and about 3.5% of water by weight, as determined by TGA.

In embodiments, crystalline form Q of Lorecivivint may be a mixed N-methylmorpholine solvate hydrate.

In any aspect or embodiment of the present disclosure, crystalline Form Q of Lorecivivint is non-hygroscopic. Particularly, Form Q of Lorecivivint according to any aspect or embodiment is polymorphically stable at up to 100% relative humidity at room temperature for at least 7 days.

In some embodiments, the present disclosure describes a set of isostructural forms of Lorecivivint designated form Q. In some embodiments, form Q isostructural forms include, for example, Form dimethylacetamide solvate hydrate, preferably form Q mono dimethylacetamide solvate mono hydrate and/or form Q N-methylmorpholine solvate hydrate.

In embodiments, crystalline form Q may be polymorphically pure.

The above crystalline polymorphs can be used to prepare other crystalline polymorphs of Lorecivivint, Lorecivivint salts and their solid state forms.

The present disclosure encompasses a process for preparing other solid state forms of Lorecivivint, Lorecivivint salts and solid state forms thereof. The process includes preparing Lorecivivint or the solid state form of Lorecivivint by the processes of the present disclosure, and converting that form to said other form of Lorecivivint or Lorecivivint salt.

The present disclosure provides the above described crystalline polymorphs of Lorecivivint for use in the preparation of pharmaceutical compositions comprising Lorecivivint and/or crystalline polymorphs thereof.

The present disclosure also encompasses the use of crystalline polymorphs of Lorecivivint of the present disclosure for the preparation of pharmaceutical compositions of crystalline polymorph Lorecivivint and/or crystalline polymorphs thereof.

In any aspect or embodiment of the present disclosure, any of the solid state forms of Lorecivivint described herein may be polymorphically pure or may be substantially free of any other solid state forms of the subject compound. In any aspect or embodiment of the present disclosure, any of the solid state forms of Lorecivivint may contain: about 20% (w/w) or less, about 10% (w/w) or less, about 5% (w/w) or less, about 2% (w/w) or less, about 1% (w/w) or less, about 0.5% (w/w) or less, about 0.2% (w/w) or less, about 0.1% (w/w) or less, or about 0%, of any other solid state forms of the subject compound, preferably as measured by XRPD. Such forms include, for example, other crystalline forms of Lorecivivint and/or amorphous Lorecivivint. Thus, any of the disclosed crystalline forms of Lorecivivint described herein may be substantially free of any other solid state forms of the subject compound, and may contain greater than about 80% (w/w), greater than about 90% (w/w), greater than about 95% (w/w), greater than about 98% (w/w), greater than about 99% (w/w), or about 100% of the solid state form of the Lorecivivint.

The present disclosure provides a process for preparation of form Q of Lorecivivint wherein the process comprises:

a) providing Lorecivivint in dimethylacetamide or a mixture of dimethylacetamide and one or more solvents;
b) optionally heating the reaction mixture, preferably to a temperature of about 70° C. to about 100° C. to obtain dissolution;
c) optionally cooling;
d) adding water and optionally stirring the reaction mixture;
e) optionally separating the precipitate; and
f) optionally washing or drying the precipitate.

The present disclosure provides a process for preparation of form Q of Lorecivivint wherein the process comprises:

a) providing Lorecivivint in dimethylacetamide or in a mixture of dimethylacetamide and one or more solvents;
b) heating the reaction mixture, preferably to a temperature of about 70° C. to about 100° C. to obtain dissolution;
c) optionally cooling the reaction mixture to Room Temperature;
d) adding water and optionally stirring the reaction mixture, for example at room temperature (optionally for about 0.5 to about 8 hours, about 1 to about 6 hours, or about 2 to about 4 hours);
e) optionally separating the precipitate (optionally by filtration or by centrifuge, optionally by centrifuge); and
f) optionally washing and/or drying the precipitate.

In a particular embodiment, the disclosure relates to a process for preparation of form Q of Lorecivivint wherein the process comprises:

a) providing Lorecivivint in dimethylacetamide;
b) heating to obtain dissolution, preferably to a temperature of about 70° C. to about 100° C. to obtain dissolution;
c) cooling to a temperature of about 15 to about 30° C.;
d) adding water optionally stirring the reaction mixture, optionally for about 1 to about 10 hours, about 2 to about 5 hours;

e) optionally separating the precipitate (optionally by filtration or by centrifuge, optionally by filtration); and f) optionally washing and/or drying the precipitate.

In any of the herein described processes for preparing Form Q of Lorecivivint, the dimethylacetamide may be used in an amount of: about 5 ml to about 20 ml per gram of Lorecivivint, about 7 ml to about 18 ml per gram of Lorecivivint, about 9 ml to about 15 ml per gram of Lorecivivint, or about 12 ml per gram of Lorecivivint.

In any of the herein described processes for preparing Form Q of Lorecivivint the water in step (d) may be used in an amount of about 5 ml to about 20 ml per gram of Lorecivivint, about 7 ml to about 18 ml per gram of Lorecivivint, about 9 ml to about 15 ml per gram of Lorecivivint, or about 12 ml per gram of Lorecivivint.

In any of the herein described processes for preparation of form Q of Lorecivivint the volume ratio of water:dimethylacetamide may be about 5:1 to about 0.5:1, about 3:1 to about 0.7:1, about 2:1 to about 0.8:1, about 1:1.

The present disclosure provides a process for preparation of form Q of Lorecivivint wherein the process comprises:

a) providing Lorecivivint in N-methylmorpholine or a mixture of N-methylmorpholine and one or more solvents;

b) optionally heating the reaction mixture, preferably to a temperature of about 70° C. to about 110° C. to obtain dissolution;

c) optionally cooling;

d) adding water and optionally stirring the reaction mixture;

e) optionally separating the precipitate; and f) optionally washing or drying the precipitate.

The present disclosure provides a process for preparation of form Q of Lorecivivint wherein the process comprises:

a) providing Lorecivivint in N-methylmorpholine or in a mixture of N-methylmorpholine and one or more solvents;

b) heating the reaction mixture, preferably to a temperature of about 70° C. to about 110° C. to obtain dissolution;

c) optionally cooling the reaction mixture to room temperature;

d) adding water and optionally stirring the reaction mixture, for example at room temperature, optionally for about 0.1 to about 6 hours, about 0.1 to about 3 hours;

e) optionally separating the precipitate (optionally by filtration or by centrifuge, optionally by centrifuge); and f) optionally washing and/or drying the precipitate.

In a particular embodiment, the disclosure relates to a process for preparation of form Q of Lorecivivint wherein the process comprises:

a) providing Lorecivivint in N-methylmorpholine;

b) heating to obtain dissolution, preferably to a temperature of about 70° C. to about 110° C. to obtain dissolution;

c) cooling to a temperature of about 15 to about 30° C.;

d) adding water optionally stirring the reaction mixture (optionally for about 0.1 to about 6 hours, about 0.1 to about 3 hours;

e) optionally separating the precipitate (optionally by filtration or by centrifuge, optionally by filtration); and f) optionally washing and/or drying the precipitate.

In any of the herein described processes for preparing Form Q of Lorecivivint, the N-methylmorpholine may be used in an amount of: about 5 ml to about 20 ml per gram of Lorecivivint, about 7 ml to about 18 ml per gram of Lorecivivint, about 9 ml to about 15 ml per gram of Lorecivivint, or about 12 ml per gram of Lorecivivint.

In any of the herein described processes for preparing Form Q of Lorecivivint the water in step (d) may be used in an amount of about 5 ml to about 20 ml per gram of Lorecivivint, about 7 ml to about 18 ml per gram of Lorecivivint, about 9 ml to about 15 ml per gram of Lorecivivint, or about 12 ml per gram of Lorecivivint.

In any of the herein described processes for preparation of form Q of Lorecivivint the volume ratio of water:N-methylmorpholine may be about 5:1 to about 0.5:1, about 3:1 to about 0.7:1, about 2:1 to about 0.8:1, about 1:1.

The present disclosure includes processes for preparing the above mentioned pharmaceutical compositions. The processes include combining any one or a combination of the crystalline polymorphs of Lorecivivint of the present disclosure with at least one pharmaceutically acceptable excipient.

Pharmaceutical combinations or formulations of the present disclosure contain any one or a combination of the solid state forms of Lorecivivint of the present disclosure. In addition to the active ingredient, the pharmaceutical formulations of the present disclosure can contain one or more excipients. Excipients are added to the formulation for a variety of purposes.

Diluents increase the bulk of a solid pharmaceutical composition, and can make a pharmaceutical dosage form containing the composition easier for the patient and caregiver to handle. Diluents for solid compositions include, for example, microcrystalline cellulose (e.g., Avicel®), microfine cellulose, lactose, starch, pregelatinized starch, calcium carbonate, calcium sulfate, sugar, dextrates, dextrin, dextrose, dibasic calcium phosphate dihydrate, tribasic calcium phosphate, kaolin, magnesium carbonate, magnesium oxide, maltodextrin, mannitol, polymethacrylates (e.g., Eudragit®), potassium chloride, powdered cellulose, sodium chloride, sorbitol, and talc.

Solid pharmaceutical compositions that are compacted into a dosage form, such as a tablet, can include excipients whose functions include helping to bind the active ingredient and other excipients together after compression. Binders for solid pharmaceutical compositions include acacia, alginic acid, carbomer (e.g. carbopol), carboxymethylcellulose sodium, dextrin, ethyl cellulose, gelatin, guar gum, hydrogenated vegetable oil, hydroxyethyl cellulose, hydroxypropyl cellulose (e.g. Klucel®), hydroxypropyl methyl cellulose (e.g. Methocel®), liquid glucose, magnesium aluminum silicate, maltodextrin, methylcellulose, polymethacrylates, povidone (e.g. Kollidon®, Plasdone®), pregelatinized starch, sodium alginate, and starch.

The dissolution rate of a compacted solid pharmaceutical composition in the patient's stomach can be increased by the addition of a disintegrant to the composition. Disintegrants include alginic acid, carboxymethylcellulose calcium, carboxymethylcellulose sodium (e.g., Ac-Di-Sol®, Primellose®), colloidal silicon dioxide, croscarmellose sodium, crospovidone (e.g., Kollidon®, Polyplasdone®), guar gum, magnesium aluminum silicate, methyl cellulose, microcrystalline cellulose, polacrilin potassium, powdered cellulose, pregelatinized starch, sodium alginate, sodium starch glycolate (e.g., Explotab®), and starch.

Glidants can be added to improve the flowability of a non-compacted solid composition and to improve the accuracy of dosing. Excipients that can function as glidants include colloidal silicon dioxide, magnesium trisilicate, powdered cellulose, starch, talc, and tribasic calcium phosphate.

When a dosage form such as a tablet is made by the compaction of a powdered composition, the composition is subjected to pressure from a punch and dye. Some excipients and active ingredients have a tendency to adhere to the surfaces of the punch and dye, which can cause the product to have pitting and other surface irregularities. A lubricant can be added to the composition to reduce adhesion and ease the release of the product from the dye. Lubricants include magnesium stearate, calcium stearate, glyceryl monostearate, glyceryl palmitostearate, hydrogenated castor oil, hydrogenated vegetable oil, mineral oil, polyethylene glycol, sodium benzoate, sodium lauryl sulfate, sodium stearyl fumarate, stearic acid, talc, and zinc stearate.

Flavoring agents and flavor enhancers make the dosage form more palatable to the patient. Common flavoring agents and flavor enhancers for pharmaceutical products that can be included in the composition of the present disclosure include maltol, vanillin, ethyl vanillin, menthol, citric acid, fumaric acid, ethyl maltol, and tartaric acid.

Solid and liquid compositions can also be dyed using any pharmaceutically acceptable colorant to improve their appearance and/or facilitate patient identification of the product and unit dosage level.

In liquid pharmaceutical compositions of the present invention, Lorecivivint and any other solid excipients can be dissolved or suspended in a liquid carrier such as water, vegetable oil, alcohol, polyethylene glycol, propylene glycol, or glycerin.

Liquid pharmaceutical compositions can contain emulsifying agents to disperse uniformly throughout the composition an active ingredient or other excipient that is not soluble in the liquid carrier. Emulsifying agents that can be useful in liquid compositions of the present invention include, for example, gelatin, egg yolk, casein, cholesterol, acacia, tragacanth, chondrus, pectin, methyl cellulose, carbomer, cetostearyl alcohol, and cetyl alcohol.

Liquid pharmaceutical compositions of the present invention can also contain a viscosity enhancing agent to improve the mouth-feel of the product and/or coat the lining of the gastrointestinal tract. Such agents include acacia, alginic acid bentonite, carbomer, carboxymethylcellulose calcium or sodium, cetostearyl alcohol, methyl cellulose, ethylcellulose, gelatin guar gum, hydroxyethyl cellulose, hydroxypropyl cellulose, hydroxypropyl methyl cellulose, maltodextrin, polyvinyl alcohol, povidone, propylene carbonate, propylene glycol alginate, sodium alginate, sodium starch glycolate, starch tragacanth, xanthan gum and combinations thereof.

Sweetening agents such as sorbitol, saccharin, sodium saccharin, sucrose, aspartame, fructose, mannitol, and invert sugar can be added to improve the taste.

Preservatives and chelating agents such as alcohol, sodium benzoate, butylated hydroxyl toluene, butylated hydroxyanisole, and ethylenediamine tetraacetic acid can be added at levels safe for ingestion to improve storage stability.

According to the present disclosure, a liquid composition can also contain a buffer such as gluconic acid, lactic acid, citric acid, or acetic acid, sodium gluconate, sodium lactate, sodium citrate, or sodium acetate. Selection of excipients and the amounts used can be readily determined by the formulation scientist based upon experience and consideration of standard procedures and reference works in the field.

The solid compositions of the present disclosure include powders, granulates, aggregates, and compacted compositions. The dosages include dosages suitable for oral, buccal, rectal, parenteral (including subcutaneous, intramuscular, and intravenous), inhalant, and ophthalmic administration. Although the most suitable administration in any given case will depend on the nature and severity of the condition being treated, in embodiments the route of administration is oral. The dosages can be conveniently presented in unit dosage form and prepared by any of the methods well-known in the pharmaceutical arts.

Dosage forms include solid dosage forms like tablets, powders, capsules, suppositories, sachets, troches, and lozenges, as well as liquid syrups, suspensions, and elixirs.

The dosage form of the present disclosure can be a capsule containing the composition, such as a powdered or granulated solid composition of the disclosure, within either a hard or soft shell. The shell can be made from gelatin and optionally contain a plasticizer such as glycerin and/or sorbitol, an opacifying agent and/or colorant.

The active ingredient and excipients can be formulated into compositions and dosage forms according to methods known in the art.

A composition for tableting or capsule filling can be prepared by wet granulation. In wet granulation, some or all of the active ingredients and excipients in powder form are blended and then further mixed in the presence of a liquid, typically water, that causes the powders to clump into granules. The granulate is screened and/or milled, dried, and then screened and/or milled to the desired particle size. The granulate can then be tableted, or other excipients can be added prior to tableting, such as a glidant and/or a lubricant.

A tableting composition can be prepared conventionally by dry blending. For example, the blended composition of the actives and excipients can be compacted into a slug or a sheet and then comminuted into compacted granules. The compacted granules can subsequently be compressed into a tablet.

As an alternative to dry granulation, a blended composition can be compressed directly into a compacted dosage form using direct compression techniques. Direct compression produces a more uniform tablet without granules. Excipients that are particularly well suited for direct compression tableting include microcrystalline cellulose, spray dried lactose, dicalcium phosphate dihydrate, and colloidal silica. The proper use of these and other excipients in direct compression tableting is known to those in the art with experience and skill in particular formulation challenges of direct compression tableting.

A capsule filling of the present disclosure can include any of the aforementioned blends and granulates that were described with reference to tableting, but they are not subjected to a final tableting step.

A pharmaceutical formulation of Lorecivivint can be administered. Lorecivivint may be formulated for administration to a mammal, in embodiments to a human, by injection. Lorecivivint can be formulated, for example, as a viscous liquid solution or suspension, such as a clear solution, for injection. The formulation can contain one or more solvents. A suitable solvent can be selected by considering the solvent's physical and chemical stability at various pH levels, viscosity (which would allow for syringeability), fluidity, boiling point, miscibility, and purity. Suitable solvents include alcohol USP, benzyl alcohol NF, benzyl benzoate USP, and Castor oil USP. Additional substances can be added to the formulation such as buffers, solubilizers, and antioxidants, among others. Ansel et al., Pharmaceutical Dosage Forms and Drug Delivery Systems, 7th ed.

The crystalline polymorphs of Lorecivivint and the pharmaceutical compositions and/or formulations of Lorecivivint of the present disclosure can be used as medicaments, in embodiments in the treatment of knee osteoarthritis.

The present disclosure also provides methods of treating knee osteoarthritis. by administering a therapeutically effective amount of any one or a combination of the crystalline polymorphs of Lorecivivint of the present disclosure, or at least one of the above pharmaceutical compositions and/or formulations, to a subject in need of the treatment.

Having thus described the disclosure with reference to particular preferred embodiments and illustrative examples, those in the art can appreciate modifications to the disclosure as described and illustrated that do not depart from the spirit and scope of the disclosure as disclosed in the specification. The Examples are set forth to aid in understanding the disclosure but are not intended to, and should not be construed to limit its scope in any way.

Powder X-Ray Diffraction ("XRPD") Method

Powder X-ray Diffraction was performed on an X-Ray powder diffractometer PanAlytical X'pert Pro; CuKα radiation (λ=1.54187 Å); X'Celerator detector with active length 2.122 degrees 2-theta; laboratory temperature 25±3° C.; zero background sample holders. Prior to analysis, the samples were gently ground using a mortar and pestle to obtain a fine powder. The ground sample was adjusted into a cavity of the sample holder and the surface of the sample was smoothed using a cover glass.

Measurement parameters:

Scan range: 3-40 degrees 2-theta
Scan mode: continuous
Step size: 0.0167 degrees
Step size: 42 s
Sample spin: 60 rpm
Sample holder: zero background silicon plate $^{11}C$ CP/MAS NMR Method:

$^{13}C$ CP/MAS NMR spectra were measured at 125 MHz using Bruker Avance 500 WB/US NMR spectrometer (Karlsruhe, Germany, 2003) at magic angle spinning (MAS) frequency $\omega_r/2\pi$=11 kHz. In all cases finely powdered samples were placed into 4 mm $ZrO_2$ rotors and the standard CPMAS pulse program was used. During acquisition of the data the high-power dipolar decoupling TPPM (two-pulse phase-modulated) was applied. The number of scans was 2048, recycle delay was 4 seconds. Taking into account frictional heating of the samples during fast rotation all NMR experiments were performed at 293 K (precise temperature calibration was performed).

The $^{13}C$ scale was calibrated with glycine as external standard (176.03 ppm).

TGA Method:

Equipment: TA Discovery;
Crucibles: Aluminum, 100 μl;
Heating range: 20-250° C.;
Heating rate: 10° C./min;
Purging gas: Nitrogen;
Purging gas flow: 25 ml/min.

EXAMPLES

Preparation of Starting Materials

Lorecivivint can be prepared according to methods known from the literature, for example International Publication No. WO 2017/210407.

Example 1: Preparation of Lorecivivint Form C

Lorecivivint (80 mg) was suspended in a mixture dichloromethane:MeOH (10:3; 13 ml), slightly heated to obtain a clear solution. Then the volume was reduced by fast evaporation (with heating to about 35° C.) by a factor of about 8.5 (to a final volume of about 1.5 ml). The solution was stirred at room temperature and crystals were formed. The suspension was stirred at room temperature for 2 hours, filtered and dried up on the filter for 15 minutes. The obtained solid was analysed by XRPD and the XRPD pattern is presented in FIG. 1.

Example 2: Preparation of Lorecivivint Form F

Lorecivivint (300 mg) was dissolved in mixture DCM: MeOH (10:3; 80 ml). Volume was reduced by fast evaporation (with heating to about 35° C.) by a factor of about 8 (to a final volume of about 11 ml). The solution was cooled down to 5° C., stirring for about 1 hour and filtered. The obtained solid was dried under nitrogen and vacuum at temperature of about 75° C. for about 12 hours. The obtained solid was analysed by XRPD and the XRPD pattern is presented in FIG. 2.

Example 3: Preparation of Lorecivivint Form H

Lorecivivint (80 mg) was suspended in 1,4-dioxane (10 ml) and heated up to 80° C., then water was added (5 ml). The solid phase was dissolved by heating to 95° C. The clear solution was cooled down to 5° C. (rate −1° C./min). The product started to crystallize at temperature of about 40° C. The suspension was stirred for 1 hour at 5° C., filtered and dried up on the filter at room temperature. The obtained material was analyzed by XRPD and the XRPD pattern is presented in FIG. 3.

Example 4: Preparation of Amorphous Lorecivivint

Lorecivivint (1.5 grams) was dissolved in a mixture of dichloromethane:methanol (400 ml; 10:3) by heating to 40° C. Volume was reduced (to 18 grams). Solid phase was filtered out and the filtrate was evaporated to dryness. The obtained solid was analyzed by XRPD and the XRPD pattern is presented in FIG. 4.

Example 5: Preparation of Lorecivivint Form Q

Procedure a (Mono Dimethylacetamide Solvate Mono Hydrate)

Lorecivivint (500 mg) was dissolved in dimethylacetamide (6 ml) by heating to 90° C. during a period of about 30 minutes. Lorecivivint was dissolved around 75° C. The clear solution was cooled down to a temperature of about 20° C. during a period of about 1 hour. Then water (6 ml) was added dropwise. Precipitation occurred within seconds. The suspension was stirred for about 4 hours at room temperature. The suspension was filtered and dried under vacuum for about 1 hour at room temperature. The obtained solid was analysed by XPRD and the XRPD pattern is presented in FIG. 5.

Procedure B (Mono Dimethylacetamide Solvate Mono Hydrate)

Lorecivivint (2 grams) was dissolved in dimethylacetamide (25 ml) by heating to 80° C. during a period of about 30 minutes. Lorecivivint was dissolved around 75° C. The clear solution was cooled down to a temperature of about 20° C. during a period of about 1 hour. Then water (25 ml) was added dropwise during a period of about 5 minutes. Precipitation occurred within seconds. The suspension was stirred for about 3 hours at room temperature. The suspension was filtered and dried under vacuum and stream of nitrogen for about 4 hours at room temperature. The obtained solid was analysed by XPRD and identified as Form Q of Lorecivivint.

Procedure C (N-Methylmorpholine Solvate Hydrate)

Lorecivivint (200 mg) was dissolved in N-Methylmorpholine (2.5 ml) by heating to 90° C. during a period of about 30 minutes. The clear solution was cooled down to a temperature of about 20° C. during a period of about 1 hour. The clear solution was added dropwise into water (2.5 ml). Precipitation immediately occurred. The suspension was stirred for about 3 hours at room temperature. The suspension was filtered and dried under vacuum for about 1 hour at room temperature. The obtained solid was analysed by XPRD and the XRPD pattern is presented in FIG. 9.

Procedure D (Mono Dimethylacetamide Solvate Mono Hydrate)

Lorecivivint (4.5 grams) was dissolved in dimethylacetamide (56 ml) by heating to 80° C. during a period of about 30 minutes. Lorecivivint was dissolved around 75° C. The clear solution was cooled down (controlled) to a temperature of about 20° C. during a period of about 1 hour. Then water (56 ml) was added dropwise. Precipitation occurred within seconds. The suspension was stirred for about 3 hours at room temperature. The suspension was filtered and dried under vacuum and stream of nitrogen for about 1.5 hours at room temperature. The obtained solid (5.26 grams) was analysed by XRPD and identified as Form Q of Lorecivivint.

Example 6: Unit Cell Parameters of Form Q

Preparation of sample for powder diffraction data analysis: Lorecivivint (500 mg) was suspended in 6 ml of dimethylacetamide and heated up to 90° C. during 1 hour. Lorecivivint was dissolved at 75° C. The clear solution was cooled down (controlled) to 25° C. during 1 hour. 6 ml of water was added dropwise at RT and the system immediately precipitated. The suspension was stirred for 4 hours at room temperature. Lorecivivint form Q was ground and placed to the 0.5 mm borosilicate-glass capillary. Powder data were collected using the Debye-Scherrer transmission configuration on the powder diffractometer SmartLab Rigaku using CuKα1 radiation (primary monochromator used). The reflection position was determined in DASH software. Indexation was done in DICVOL06 software. The final Rietveld refinement was done in Jana software with restrains on all bonds and valance angles.

| Unit cell parameters | Crystal structure |
|---|---|
| Cell length a | 13.4972 Å |
| Cell length b | 19.5568 Å |
| Cell length c | 11.7005 Å |
| Cell angle alpha | 90° |
| Cell angle beta | 90.7443° |
| Cell angle gamma | 90° |
| Cell volume | 3088.2 $Å^3$ |
| Symmetry cell setting | Monoclinic |
| Symmetry space group name | $P\,2_1/c$ |
| Cell measurement temperature | 298K |

The invention claimed is:

1. A crystalline form of Lorecivivint designated form Q, which is characterized by data selected from one or more of the following:

(a) an XRPD pattern having peaks at 10.9, 17.2, 21.9, 22.9 and 25.2 degrees 2-theta±0.2 degrees 2-theta;

(b) an XRPD pattern having peaks at 10.9, 17.2, 21.9, 22.9 and 25.2 degrees 2-theta±0.2 degrees 2-theta, and also having any one, two, three, four or five additional peaks selected from 8.8, 11.8, 13.1, 18.9 and 24.1 degrees 2-theta±0.2 degrees 2-theta;

(c) an X-ray powder diffraction pattern having peaks at 8.8, 10.9, 11.8, 13.1, 17.2, 18.9, 21.9, 22.9, 24.1 and 25.2 degrees 2-theta±0.2 degrees 2-theta;

(d) a solid state $^{13}C$ NMR spectrum with characteristic peaks at 173.3, 149.9, 134.0, 131.5 and 118.2 ppm±0.2 ppm;

(e) a solid state $^{13}C$ NMR spectrum having the following chemical shift absolute differences from reference peak at 108.0 ppm ±1 ppm: 65.3, 41.9, 26.0, 23.5 and 10.2 ppm±0.1 ppm;

(f) the following unit cell data:

| | |
|---|---|
| cell_length_a | 13.497 Å |
| cell_length_b | 19.557 Å |
| cell_length_c | 11.701 Å |
| cell_angle_beta | 90.744° |
| Symmetry space group name | $P2_1/c$ |

and (g) combinations of these data.

2. A crystalline product according to claim 1, wherein the crystalline form is a mixed solvate hydrate.

3. A crystalline form according to claim 1, wherein the form is a dimethylacetamide solvate hydrate.

4. A crystalline form according to claim 1, wherein the form is a mono dimethylacetamide solvate mono hydrate.

5. A crystalline form according to claim 1, wherein the form contains about 13% to about 17% of dimethylacetamide and about 2% to about 5% of water, as determined by TGA.

6. A crystalline product according to claim 1, wherein the crystalline product is a N-methylmorpholine solvate hydrate.

7. A crystalline product according to claim 1, which contains no more than about 20% of any other crystalline forms of Lorecivivint.

8. A crystalline product according to claim 1, which contains no more than about 20% of amorphous Lorecivivint.

9. A crystalline product according to claim 1, which is non-hygroscopic.

10. A pharmaceutical composition comprising a crystalline product according to claim 1 and at least one pharmaceutically acceptable excipient.

11. A process for preparing a pharmaceutical composition comprising combining a crystalline form according to claim 1 with at least one pharmaceutically acceptable excipient.

12. A medicament comprising the crystalline product according to claim 1.

13. A method of treating knee osteoarthritis, comprising administering a therapeutically effective amount of a crystalline product according to claim 1 to a subject in need of the treatment.

* * * * *